United States Patent [19]

De Kany et al.

[11] Patent Number: 5,091,411
[45] Date of Patent: Feb. 25, 1992

[54] PSEUDO-PRIMYCIN COMPLEXES, COMPONENTS AND ACID ADDITION SALTS THEREOF AS WELL AS A PROCESS FOR THE PREPARATION OF SAME

[75] Inventors: Gyula De Kany; Judit Frank; István Pelczer; Gabor Kulcsar; Eniko Schreiner, all of Budapest, Hungary

[73] Assignee: Chinoin Gyogyszer es Vegyeszeti Termekek Gyara R.T., Budapest, Hungary

[21] Appl. No.: 365,939

[22] Filed: Jun. 14, 1989

[30] Foreign Application Priority Data

Jun. 14, 1988 [HU] Hungary ............................. 3036/88

[51] Int. Cl.$^5$ ................ C07D 313/00; A61K 31/335; C07H 17/08
[52] U.S. Cl. .................... 514/450; 514/25; 549/271; 536/6.5
[58] Field of Search .............. 549/271; 536/6.5; 514/25, 450

[56] References Cited

FOREIGN PATENT DOCUMENTS 0178909 10/1984 European Pat. Off. ............ 549/271

Primary Examiner—C. Warren Ivy
Assistant Examiner—Celia Chang
Attorney, Agent, or Firm—Herbert Dubno; Jonathan Myers

[57] ABSTRACT

The invention relates to antibacterial pseudo-primycin complexes of formula (I)

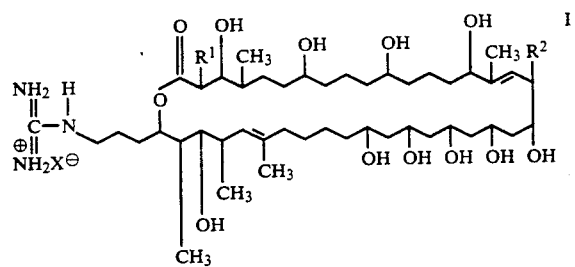

to the components and acid addition salts thereof, as well as to the preparation of these compounds and to the pharmaceutical compositions containing said compounds as active ingredient.

In the formula (I) $R^1$ is butyl, pentyl or hexyl, $R^2$ is hydrogen, hydroxyl or O-arabinose and X is organic or inorganic acid ion.

14 Claims, No Drawings

PSEUDO-PRIMYCIN COMPLEXES, COMPONENTS AND ACID ADDITION SALTS THEREOF AS WELL AS A PROCESS FOR THE PREPARATION OF SAME

FIELD OF THE INVENTION

The invention relates to pseudo-primycin complexes and to components and to acid addition salts thereof as well as to a process for the preparation of same.

The invention further relates to pharmaceutical compositions containing said pseudo-primycin complex and/or any components and/or acid addition salts thereof.

BACKGROUND OF THE INVENTION

Primycin is a macrolide antibiotic (Nature, 174,1105/1954) showing antibacterial activity and it is the active ingredient of the commercially available EBRIMYCIN ® gel. It exhibits an outstanding antibacterial activity and no resistance has developed against it yet. On the basis of these advantageous properties it is widely used, however, at the present, it is formulated only as an alcoholic gel and used for surfacial treatments.

The development of other pharmaceutical formulations is very limited as primycin is insoluble or only poorly soluble in water and in different organic solvents.

OBJECT OF THE INVENTION

The object of our invention is to provide a process by which the solubility and so the utility of primycin can be improved.

SUMMARY OF THE INVENTION

It has been surprisingly found that primycin, upon treatment with different basic materials, nucleophilic materials and/or metal compounds, may be converted into a new form (a new compound) which is well soluble in water and/or organic solvents and in addition it possesses outstanding gelling properties. The reaction which takes place is $C_{35}-C_{37}$ translactonization, i.e. the primycin ring originally having 35 carbon atoms is transformed into a ring having 37 carbon atoms. The primycin obtained in this reaction is called pseudo-primycin.

The pseudo-primycin similarly to the starting primycin is a complex too, i.e. it also contains different components, which can be separated by the methods used for the separation of primycin (see HUP No. 196 425)..

Alternatively the components of the pseudo-primycin can also be prepared by the translactonisation reaction of the individual isolated components of primycin. All the so far known primycin-components react similarly.

According to our experiments pseudo-primycin as well as its components exhibit antibacterial activity and can be used for the preparation of pharmaceutical compositions containing the active ingredient in a higher dose. Due to their new structure, resistance has not been developed against them yet.

According to the aforementioned the present invention relates to a pseudo-primycin complex of formula (I) and/or their components and acid addition salts thereof as well as to a process for the preparation of same. In the formula (I)

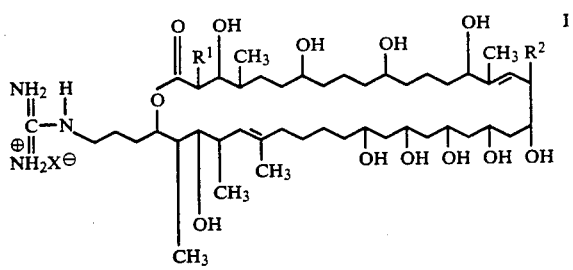

$R^1$ represents butyl, hexyl or pentyl,
$R^2$ represents hydrogen, hydroxyl or O-arabinose,
X represents an inorganic acid ion, preferably sulfate ion or organic acid ion preferably acetate ion.

According to our process
a) for the preparation of a pseudo-primycin complex of formula (I) a primycin complex of formula (II)

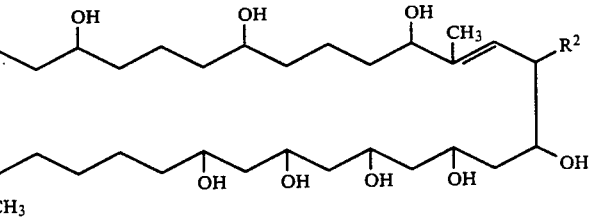

wherein
$R^1$, $R^2$ and X are the same as mentioned above is reacted with a charged basic material or with a chargeless compound to carry out a $C_{35}-C_{37}$ translactonization reaction, b) for the preparation of the components of the pseudo-primycin complex the translactonization is carried out with the components of a primycin complex of formula (II), or c) for the preparation of the components of a pseudo-primycin complex a pseudo-primycin complex of the formula (I) is separated by chromatography.

In the process according to the invention any primycin salt may be used as starting material, however the preferred compound is the primycin sulfate prepared by fermentation or primycin acetate obtained from the sulfate. The preparation of primycin acetate and other primycin salts different from the sulfate is described in HUP No. 196,822.

The translactonization is an equilibrium reaction wherein generally a 1:1 mixture of the products is obtained and it is carried out by using either materials having a charge or chargeless compounds.

The materials having a charge are mainly salts decomposed to ions, the anions of which may be organic e.g. alcoholate, preferably methylate, ethylate, or phenolate or carboxylate, preferably acetate, formiate, chloroacetate, succinate, benzoate, or the anions may be inorganic e.g. carbonate, hydrogen carbonate, sulfate, sulfide, phosphate, dihydrogen phosphate, nitrate, nitrite, cyanide, chloride, bromide, fluoride. The cations may be alkali metals, preferably sodium, potassium or alkali earth metals e.g. magnesium or transition metals, preferably iron.

In addition the following materials may also be used as materials having a charge: quaternary ammonium salts, preferably tetrabutyl ammonium bromide, or nucleophilic materials, preferably ion exchange resins, e.g. Amberlite IRA 401.

The chargeless compound used in the translactonization reaction can be selected from metal oxides and hydroxides, preferably sodium hydroxide, barium hydroxide and magnesium hydroxide, further organic bases, preferably diethylamine, triethylamine, aniline, further nitrogen- or oxygen- containing heterocyclic compounds, preferably pyridine, quinoline, piperazine, imidazole, dioxan.

The translactonization reaction is carried out in aqueous and/or organic solvent medium. As organic solvents protic solvents, e.g. aliphatic alcohols having 1-4 carbon atoms, preferably methyl alcohol, ethyl alcohol, n-butanol, halogenated hydrocarbons, preferably chloroform, or aprotic solvents, e.g. ether, or organic bases, e.g. diethylamine, pyridine, acetonitrile, dimethyl formamide are used. The preferred compounds are the aliphatic alcohols having 1-4 carbon atoms alone or in an aqueous mixture.

The reaction may be carried out at room temperature (20°-22° C.), however an elevated temperature e.g. the reflux temperature may also be used to achieve a higher reaction rate.

According to a preferred embodiment of our process the starting primycin salt is, if desired, converted into acetate, then pseudo-primycin acetate is prepared according to the above described translactonization reaction, the unreacted primycin acetate is separated from the pseudo-primycin acetate by a treatment with a suitable organic material, preferably with ethyl formiate. The precipitated primycin acetate is filtered off and the pseudo-primycin is isolated from the filtrate in the form of the acetate or if desired—after adding the corresponding acid—in the form of other salts, e.g. sulfate. The isolation is carried out preferably with ether and/or with water or acetonitrile, thereafter the product obtained is filtered and dried.

In variant b) of the process according to the invention the separated, individual components of the primycin complex are used for the translatonization and so the corresponding components of the pseudo-primycin are obtained. The reaction is carried out as described above for variant a).

According to variant c) of our process the components of the pseudo-primycin are obtained by the chromatographic separation of the pseudo-primycin complex obtained by variant a). The separation may be carried out by column or thin layer chromatography. As the solubility of the pseudo-primycin is better than that of the primycin, the chromatographic separation can generally easily be carried out by a simple column chromatography.

According to our invention the column chromatographic separation is preferably carried out by using silica gel (e.g. Kieselgel 60) filled into the column suspended in the used eluent. The primycin salt to be separated is also applied to the column in the form of a solution in the used eluent. The eluent used for the development may be the mixture of water and different organic solvent(s). It has been found that the presence of an organic acid in the eluent improves the efficacy of the separation. As organic solvents preferably alcohol(s), e.g. methanol, ethanol, butanol or halogenated solvents, e.g. chloroform, dichloromethane etc., and as organic acids preferably acetic acid are used. The preferred solvent system is the lower phase of the chloroform:methanol:acetic acid:water=9:6:3:4 mixture, stabilized with 1% by volume of methanol.

During the development the fractions containing identical materials (proved by thinlayer chromatography, TLC) are collected, and after evaporation the four components are obtained. The TLC tests are carried out on silica gel, preferably on Kieselgel 60 $F_{254}$ (Merck) or HPTLC HP-KF (Whatmann) plates using 10 μl of samples. The eluent is the 160:53:6:9:3 mixture of chloroform:methanol:formic acid:water:formaldehyde:n-butanol and for the development chlorotoluidine or ethanol containing 1% of phosphoro molybdenic acid is used.

By the chromatographic separation of the pseudo-primycin complex components similar to the components of primycin are obtained, i.e. $A_1$, $A_2$, $A_3$, $B_1$, $B_2$, $B_3$, $C_1$, $C_2$, $C_3$. The components of the pseudo-primycin complex of formula (I) are as follows:

pseudo-primycin-$A_1$, wherein $R^1$ is butyl, $R^2$ is O-arabinose and X is the same as mentioned above;

pseudo-primycin-$A_2$, wherein $R^1$ is pentyl, $R^2$ is O-arabinose and X is the same as mentioned above;

pseudo-primycin-$A_3$, wherein $R^1$ is hexyl, $R^2$ is O-arabinose and X is the same as mentioned above;

pseudo-primycin-$B_1$, wherein $R^1$ is butyl, $R^2$ is hydrogen, X is the same as mentioned above;

pseudo-primycin-$B_2$, wherein $R^1$ is pentyl, $R^2$ is hydrogen, X is the same as mentioned above;

pseudo-primycin-$B_3$, wherein $R^1$ is hexyl, $R^2$ is hydrogen, X is the same as mentioned above;

pseudo-primycin-$C_1$, wherein $R^1$ is butyl, $R^2$ is hydroxyl, X is the same as mentioned above;

pseudo-primycin-$C_2$, wherein $R^1$ is pentyl, $R^2$ is hydroxyl, X is the same as mentioned above;

pseudo-primycin-$C_3$, wherein $R^1$ is hexyl, $R^2$ is hydroxyl, X is the same as mentioned above, as well as the acid addition salts thereof.

The $R_f$-values characteristic of the components of the pseudo-primycin are as follows:

| | | |
|---|---|---|
| $A_1$ $R_f$ = 0.30 | $B_1$ $R_f$ = 0.55 | $C_1$ $R_f$ = 0.36 |
| $A_2$ $R_f$ = 0.32 | $B_2$ $R_f$ = 0.57 | $C_2$ $R_f$ = 0.38 |
| $A_3$ $R_f$ = 0.34 | $B_3$ $R_f$ = 0.59 | $C_3$ $R_f$ = 0.40 |

The solubility of the pseudo-primycin complex or the components thereof according to our invention is much better than that of the starting primycin complex and/or its components. For example the primycin acetate is practically insoluble in water, ethanol, methanol, while the solubility of pseudo-primycin-acetate in water is 5 g/10 ml, in ethanol 5 g/10 ml and in methanol 10 g/10 ml, which means a significant improvement of solubility.

The improvement of solubility of the individual pseudo-primycin components is the same as mentioned above in case of the pseudo-primycin complex, i.e. e.g. the solubility of pseudo-primycin-$A_1$-acetate is in water and in ethanol 5 g/10 ml and in methanol 10 g/10 ml. Accordingly the pseudo-primycin complex and/or its components are suitable for the preparation of pharmaceutical formulations containing a higher dose of active ingredient.

A further advantageous property of the pseudo-primycin and its components is the outstanding gellation capacity: in aqueous medium the gel formation immediately starts at the limit of the solubility and in organic solvent medium a stable gel is formed after several hours standing.

Said gellation capacity can advantageously be utilized when preparing certain pharmaceutical formulations, e.g. gels, ointments, etc.

The salts of the pseudo-primycin and/or of its components can be converted into the free compounds if desired and/or they can be transformed into an other salt.

Similarly to the original primycin complex and/or its components the pseudo-primycin complex and/or its components also exhibit antibiotical activity first of all against gram-positive bacterials but in a higher dose they are also effective against gram-negative bacteria.

Table 1

Activity spectra of pseudo-primycin complex and its components against polyresistant human phatogenic strains.

Tested strains

1.) Bacillus subtilis
2.) Bacillus cereus
3.) Bacillus licheniformis
4.) Staphylococcus aureus
5.) Staphylococcus epidermis
6.) Micrococcus strains
7.) Sporosarcina ureae Cont. of Table 1

Tested compounds

I.) Pseudo-primycin-acetate
II.) Pseudo-primycin-$A_1$-acetate
III.) Pseudo-primycin-$A_3$-acetate
IV.) Pseudo-primycin-$B_1$-acetate
V.) Pseudo-primycin-$B_3$-acetate
VI.) Pseudo-primycin-$C_1$-acetate

| | Mic values (μg/ml) Tested compounds | | | | | |
|---|---|---|---|---|---|---|
| Tested strains | I. | II. | III. | IV. | V. | VI. |
| 1. | 2.5–5 | 5–10 | 2.5 | 2.5 | 2.5 | 2.5 |
| 2. | 2.5–5 | 5–10 | 2.5 | 2.5 | 2.5 | 2.5 |
| 3. | 2.5–5 | 5–10 | 2.5 | 2.5 | 2.5 | 2.5 |
| 4. | 2.5–5 | 5–10 | 5 | 5 | 5 | 2.5 |
| 5. | 2.5–5 | 5–10 | 5 | 5 | 5 | 2.5 |
| 6. | 0.75 | 2.5 | 2.5 | 2.5 | 1 | 1–2.5 |
| 7. | 0.5 | 1 | 0.5 | 2.5 | 0.75 | 0.5 |

The toxicity of the pseudo-primycin complex and components thereof according to our invention was tested on female and male mice, the results obtained are summarized in Table 2.

Table 2

Toxicity data of pseudo-primycin complex and components thereof.

| | $LD_{50}$ values (mg/kg) | | | |
|---|---|---|---|---|
| | i.v. | | p.o. | |
| Tested compound | male | female | male | female |
| Pseudo-primycin-acetate | 17.66 | 18.78 | 1724 | 1583 |
| Pseudo-primycin-$A_1$-acetate | 13.30 | 14.75 | 937 | 806 |

The invention is illustrated in detail by the following Examples.

EXAMPLE 1

60.0 g (53.23 mmoles) of primycin-sulfate and 8.5 g (26.94 mmoles) barium hydroxide octahydrate are suspended in the mixture of 800 ml of methanol and 200 ml of water, and after a 2.5-hour boiling 20 ml of acetic acid are added and the boiling is continued for 30 minutes. Thereafter the barium sulfate is filtered off hot, the filtrate is evaporated, the oily residue is dissolved in 100 ml of methanol and 200 ml of ethyl formiate are added dropwise under stirring to the solution in about 20 minutes, at room temperature. Thereafter the unreacted primycin acetate is filtered off, the filtrate is evaporated in vacuo, the solid residue is triturated with 100 ml of diethyl ether, filtered and the white, solid powder is dried in vacuo at 70° C. The product is 26.0 g of pseudo-primycinacetate, yield: 43.3%; m.p.: 106° C.; specific rotation: +35° (in 0.2% methanolic solution)

EXAMPLE 2

60.0 g (52.77 mmoles) of primycin sulfate are suspended in 800 ml of methanol and 2.14 g (53.5 mmoles) of sodium hydroxide are added to it dissolved in 200 ml water. The suspension is boiled for 2.5 hours under stirring, thereafter 20 ml of acetic acid are added to the hot reaction mixture, the stirring is continued for 30 minutes and it is evaporated in vacuo. The residue is dissolved in 100 ml of methanol and 200 ml of ethyl formiate are added under stirring in about 20 minutes to the solution. The unreacted primycin acetate is filtered off, the filtrate is evaporated in vacuo, the residue triturated with the mixture of 450 ml of diethyl ether and 9 ml of water, the suspension thus obtained is filtered, the material obtained is dried at 70° C. in vacuo. The product is 25 g (41.6%) of pseudo-primycin acetate, m.p.: 106° C.

EXAMPLE 3

60.0 g (53.23 mmoles) of primycin sulfate are suspended in 200 ml of water containing 2.9 g (27.35 mmoles) of sodium hydroxide, 800 ml of methanol are added and boiled for 2.5 hours under stirring. Thereafter 20 ml of acetic acid are added to the solution and boiled for another 30 minutes. The reaction mixture is evaporated in vacuo, the residue is dissolved in 100 ml of methanol, the insoluble material (sodium sulfate) is filtered off and 200 ml of ethyl formiate are added dropwise to the solution under stirring about 20 minutes and the precipitated unreacted primycin acetate is filtered off. To the filtrate 33.5 ml of 2N hydrochloride are added dropwise under stirring, the pseudo-primycin sulfate obtained is filtered off and dried in vacuo. 24.5 g (40.8%) of pseudo-primycin sulfate are obtained in the form of a white powder, m.p.: 127° C., specific rotation: +26.5° (in 0.2% methanolic solution).

EXAMPLE 4

30.0 g (26.38 mmoles) of primycin acetate are suspended in 900 ml of a 2:1 mixture of methanol:water, 10 g of dry Amberlite IRA-401 (OH-form) ion-exchange resin are added and the mixture is stirred for 4 hours at 60° C. Thereafter the resin is filtered off, 10 ml of acetic acid and 100 ml of butanol are added to the filtrate and the solution is evaporated in vacuo. The residue is dissolved in 50 ml of methanol and under vigorous stirring in about 15 minutes 100 ml of ethyl formate are added dropwise to the solution at room temperature. The precipitated unreacted primycin acetate is filtered off, the filtrate is evaporated in vacuo and the residual material is triturated with diethyl ether. The suspension is filtered, the solid material dried in vacuo at 70° C. The product is 14.0 g (46.6%) of pseudo-primycin-acetate, m.p.: 106° C.

EXAMPLE 5

To the sodium-methylate solution, prepared from 0.31 g (13.48 mmoles) of sodium metal and 50 ml of methanol under anhydrous reaction conditions, 15.0 g (13.19 mmoles) of primycin acetate are added, the suspension obtained is stirred vigorously for one hour, thereafter 10 ml of acetic acid are added and the reaction mixture is evaporated in vacuo. The residue is dissolved in 250 ml of methanol under gentle heating and 50 ml of ethyl formate are added dropwise to the solution at room temperature in 10 minutes. The unreacted primycin sulfate is filtered off, the filtrate is evaporated in vacuo, the residue is triturated with the mixture of 112 ml of diethyl ether and 2.2 ml of water, the suspension is filtered and the solid material dried in vacuo at 70° C. The product is 7.0 g (46.6%) of pseudo-primycin acetate, m.p.: 106° C.

EXAMPLE 6

15.0 g (13.19 mmoles) of primycin acetate are suspended in 50 ml of methanol, 1.56 g (13.48 mmoles) of sodium phenolate are added and the suspension is stirred vigorously for one hour at 60° C. To the solution obtained 10 ml of acetic acid are added and the solvent is distilled off under reduced pressure. The residue is dissolved in 250 ml of methanol under gentle heating and 50 ml of ethyl formiate are added dropwise in about 20 minutes to the solution under stirring. The unreacted primycin acetate is filtered off; the filtrate is evaporated in vacuo; the residue is triturated with the mixture of 112 ml of diethyl ether and 2.2 ml of water. Thereafter the suspension thus obtained is filtered, and the solid material is dried in vacuo at 70° C. The product is 7.0 g (46.6%) of pseudo-primycin-acetate, m.p.: 106° C.

EXAMPLE 7

6.0 g (5.27 mmoles) of primycin-acetate are suspended in 400 ml of n-butanol and 0.49 g (6.0 mmoles) of sodium acetate are added to it. The reaction mixture is boiled under stirring for one hour, thereafter the solvent is distilled off and the residue is dissolved in 10 ml of methanol. To the solution thus obtained 20 ml of ethyl formiate are added dropwise in about 20 minutes at room temperature under stirring. Thereafter the unreacted primycin acetate is filtered off; the filtrate is evaporated under reduced pressure; and the residue is triturated with 30 ml of acetonitrile. The suspension thus obtained is filtered and the solid material is dried at 70° C. in vacuo. The product is 2.8 g (46.6%) pseudo-primycin-acetate, m.p.: 106° C.

EXAMPLE 8

6.0 g (5.27 mmoles) of primycin acetate are suspended in 400 ml of n-butanol and 6.0 mmoles of inorganic reagent, dissolving in methanol poorly, (e.g. sodium chloride, sodium sulfate, sodium sulfite, sodium bicarbonate, iron(III) phosphate, potassium nitrate, sodium nitrite, potassium bromide, potassium fluoride, magnesium oxide, sodium cyanide, sodium dihydrogen phosphate, iron(II) sulfide, etc. are added to it. The reaction mixture is boiled under stirring for one hour, 5 ml of acetic acid are added to it, thereafter the solvent is distilled off in vacuo. The residual solid material is dissolved under heating in 10 ml of methanol; the insoluble material is filtered off; and to the filtrate 20 ml ethyl formiate are added dropwise under stirring in about 20 minutes at room temperature. The unreacted primycin acetate is filtered off, the filtrate is evaporated in vacuo; and the residue is triturated with diethyl ether. The suspension thus obtained is filtered and the solid material dried in vacuo at 70° C. The product is 2.8 g (46.6%) of pseudo-primycin acetate, m.p.: 106° C.

EXAMPLE 9

60. g (5.27 mmoles) of primycin acetate are suspended in 400 ml of n-butanol; 1.0 g (3.1 mmoles) of tetrabutyl ammonium bromide is added to it, and boiled for two hours. Thereafter 5.0 ml of acetic acid are added to it and the solvent is distilled off in vacuo. The solid residue is triturated with 30 ml of chloroform; the suspension obtained is filtered; and the solid material is dissolved in 10 ml of methanol under heating. Thereafter at room temperature 20 ml of ethyl formiate are added to the solution dropwise under stirring over about 20 minutes. The unreacted primycin acetate is filtered off, the filtrate is evaporated in vacuo; and the residue is triturated with diethyl ether. The suspension obtained is filtered and dried in vacuo at 70° C. The product is 2.8 g (46.6%) of pseudo-primycin acetate m.p.: 106° C.

EXAMPLE 10

6.0 g (5.27 mmoles) of primycin acetate are suspended in the mixture of 360 ml of n-butanol and 60 ml diethylamine and boiled under stirring for 4.5 hours. Thereafter the reaction mixture is concentrated to its half in vacuo; 5 ml acetic acid are added; and the solvent is distilled off in vacuo. The residue is dissolved in 10 ml of methanol and to the solution obtained 20 ml of ethyl formiate are added dropwise under stirring at room temperature in about 20 minutes. The unreacted primycin acetate is filtered off; the filtrate is evaporated; the residue is triturated with diethyl ether; and the suspension is filtered and the solid material is dried in vacuo at 70° C. The product is 2.8 g (46.6%) of pseudo-primycin-acetate, m.p.: 106° C.

EXAMPLE 11

60.0 g (52.77 mmoles) of primycin acetate is boiled for 3.5 hours in 400 ml of pyridine, thereafter the solution thus obtained is evaporated in vacuo. The residue is washed with 2×50 ml ethanol. The ethanol is distilled off and the residue is dissolved in 100 ml of methanol and to the solution thus obtained 200 ml of ethyl formiate are added dropwise under stirring at room temperature over about 20 minutes. The unreacted primycin-acetate is filtered off; the filtrate is evaporated in vacuo;

and the residue is triturated with diethyl ether. The suspension obtained is filtered and the solid material dried in vacuo at 70° C. The product is 25 g (41.6%) of pseudo-primycin-acetate, m.p.: 106° C.

EXAMPLE 12

1.0 g (0.89 mmoles) of primycin-$A_1$-sulfate (prepared according to HUP No. 196,425) and 0.14 g (0.45 mmoles) of barium hydroxide octahydrate are suspended in the mixture of 13.5 ml of methanol and 3.5 ml of water. The reaction mixture is boiled under stirring for 2.5 hours, and after adding 0.4 ml of acetic acid the stirring is continued for 30 minutes. Thereafter the barium sulfate produced during the reaction is filtered off. The filtrate is evaporated, the oily residue is dissolved in 1.6 ml of methanol; and to the solution obtained 3.4 ml of ethyl formiate are added dropwise under stirring at room temperature over about 20 minutes. The unreacted primycin acetate is filtered off; the filtrate is evaporated in vacuo; the suspension obtained is filtered; and the white, solid material is dried in vacuo at 70° C. The product is 0.43 g (43%) of pseudo-primycin-$A_1$-acetate, m.p.: 108° C.

EXAMPLE 13

Separation of the components of pseudo-primycin by column chromatography

1.) Chromatographic separation

Sample to be separated: 6.8 g of pseudo-primycin acetate (prepared according to any of Examples 1,2,4-11) dissolved in 30 ml of eluent.

Column: 03.6 cm, length 90 cm, packed with silica gel (Kieselgel 60, Merck, particle size: 0.063-0.100 mm) suspended in the eluent.

Eluent: lower phase of the mixture of chloroform:methanol:acetic acid=9:6:3:4 stabilized with 1% by volume of methanol.

Flow rate: 1.75 ml/mixture.

Volume of the collected fractions: 10 ml

The active ingredient content of the fractions was tested by TLC.

2) TLC test

The test was carried out on Kieselgel 60 $F_{254}$ (Merck) plate using 10 μl of sample.

A mixture of chloroform:methanol:formic acid:water:formaldehyde=130:53:6:9:3:3 was used as eluent and the development was carried out by chlorotoluidin or ethanol containing 1% of phosphoromolybdenic acid.

The chromatographically identical fractions were combined, diluted with 10 ml of methanol and evaporated in vacuo. The solid residue was triturated with diethyl ether, filtered and the solid white powder was dried in vacuo at 70° C.

Thus the following components were obtained:

| Component | Weight (g) | Yield (%) | m.p. (°C.) | $/α/_D^{25x}$ (°) |
|---|---|---|---|---|
| Pseudo-primycin-$A_1$-acetate | 1.60 | 23.5 | 108 | +38.4 |
| Pseudo-primycin-$A_3$-acetate | 0.30 | 4.4 | 110 | +52.1 |
| Pseudo-primycin-$C_1$-acetate | 0.98 | 14.4 | 104 | +42.2 |
| Pseudo-primycin-$B_1$-acetate | 0.45 | 6.6 | 103 | +50.0 |
| Pseudo-primycin-$B_3$-acetate | 0.10 | 1.4 | 103 | +45.0 |

*The specific rotation was determined in 0.2% methanolic solution

What we claim is:

1. A compound of the Formula (Ia)

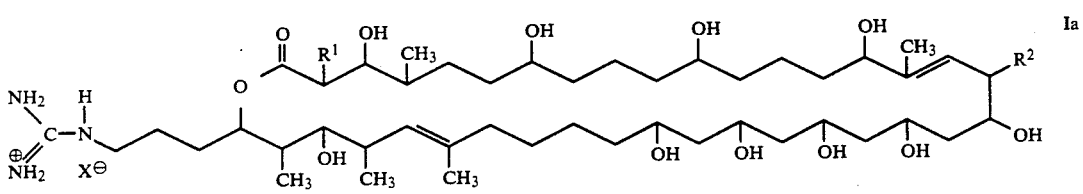

wherein
$R^1$ is butyl, pentyl or hexyl;
$R^2$ is hydrogen or hydroxyl; and
X is a pharmaceutically acceptable inorganic acid ion or organic acid ion; or a mixture thereof.

2. The compound of the Formula (Ia) defined in claim 1 selected from the group consisting of:
 (a) pseudoprimycin $B_1$, wherein $R^1$ is butyl and $R^2$ is hydrogen;
 (b) pseudoprimycin $B_3$, wherein $R^1$ is hexyl and $R^2$ is hydrogen; and
 (c) pseudoprimycin $C_1$, wherein $R^1$ is butyl and $R^2$ is hydroxyl; or a mixture thereof and in each case X is a pharmaceutically acceptable inorganic acid ion or organic acid ion.

3. Pseudoprimycin $B_1$ acetate as defined in claim 1.

4. Pseudoprimycin $B_3$ acetate as defined in claim 1.

5. The compound of the Formula (I) as defined in claim 1 which is pseudoprimycin $C_1$, wherein $R^1$ is butyl and $R^2$ is hydroxyl, and X is a pharmaceutically acceptable inorganic acid ion or organic acid ion.

6. Pseudoprimycin $C_1$ acetate as defined in claim 1.

7. An antibacterial pharmaceutical composition which comprises an antibacterially effective amount of at least one compound of the Formula (Ia) as defined in claim 1 in combination with a pharmaceutically acceptable inert carrier.

8. A method of treating a bacterial infection in a mammalian subject which comprises the step of administering to said mammalian subject an antibacterially effective amount of at least one compound of the Formula (Ia) as defined in claim 1.

9. A compound of the Formula (I)

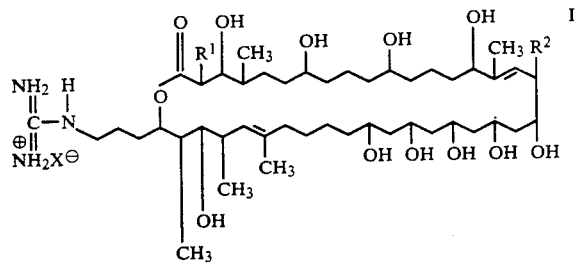

wherein $R^1$ is butyl, pentyl or hexyl;

$R^2$ is hydrogen, hydroxyl, or O-arabinose; and

X is a pharmaceutically acceptable inorganic acid ion or organic acid ion; or a mixture thereof.

10. The compound of the Formula (I) as defined in claim 9 selected from the group consisting of:
   (a) pseudoprimycin $A_1$, wherein $R^1$ is butyl and $R^2$ is O-arabinose;
   (b) pseudoprimycin $A_3$, wherein $R^1$ is hexyl and $R^2$ is O-arabinose
   (c) pseudoprimycin $B_1$, wherein $R^1$ is butyl and $R^2$ is hydrogen;
   (d) pseudoprimycin $B_3$, wherein $R^1$ is hexyl and $R^2$ is hydrogen; and
   (e) pseudoprimycin $C_1$, wherein $R^1$ is butyl and $R^2$ is hydroxyl; or a mixture thereof and in each case X is a pharmaceutically acceptable inorganic acid ion or organic acid ion.

11. Pseudoprimycin $A_1$ acetate as defined in claim 10.

12. Pseudoprimycin $A_3$ acetate as defined in claim 10.

13. An antibacterial pharmaceutical composition which comprises an antibacterially effective amount of at least one compound of the Formula (I) as defined in claim 9 in combination with a pharmaceutically acceptable inert carrier.

14. A method of treating a bacterial infection in a mammalian subject which comprises the step of administering to said mammalian subject a therapeutically effective amount of at least one compound of the Formula (I) as defined in claim 9.

* * * * *